US009186157B2

(12) United States Patent
Brunnett et al.

(10) Patent No.: US 9,186,157 B2
(45) Date of Patent: *Nov. 17, 2015

(54) HIGH SPEED SURGICAL CUTTING INSTRUMENT

(71) Applicant: Medtronic Xomed, Inc., Jacksonville, FL (US)

(72) Inventors: William C. Brunnett, Jacksonville, FL (US); Charles Stanislaus, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/060,130

(22) Filed: Oct. 22, 2013

(65) Prior Publication Data
US 2014/0046329 A1 Feb. 13, 2014

Related U.S. Application Data

(60) Continuation of application No. 12/986,356, filed on Jan. 7, 2011, now Pat. No. 8,568,415, which is a division of application No. 11/444,121, filed on May 31, 2006, now Pat. No. 7,879,037, which is a continuation-in-part of application No. 10/776,835, filed on Feb. 11, 2004, now Pat. No. 7,488,322.

(51) Int. Cl.
*A61B 17/16* (2006.01)
*A61B 17/32* (2006.01)
(Continued)

(52) U.S. Cl.
CPC ......... *A61B 17/1624* (2013.01); *A61B 17/1631* (2013.01); *A61B 17/1633* (2013.01);
(Continued)

(58) Field of Classification Search
CPC ........... A61B 17/1624; A61B 17/1631; A61B 17/1633; A61B 17/1662; A61B 17/1679; A61B 17/32002; A61B 2017/00845; A61B 2017/2904; A61B 2017/320032
USPC ........ 606/79, 84, 85, 167, 170, 180; 433/125, 433/131
See application file for complete search history.

(56) References Cited

U.S. PATENT DOCUMENTS 2,419,045 A 1/1947 Whittaker
3,976,077 A 8/1976 Kerfoot, Jr.
(Continued)

FOREIGN PATENT DOCUMENTS

DE 3609122 8/1987
EP 0634146 1/1995
(Continued)

OTHER PUBLICATIONS

Japanese Office Action for Application No. 2013-092280 mailed May 16, 2014 (2 pgs).
(Continued)

*Primary Examiner* — Pedro Philogene
*Assistant Examiner* — David Comstock
(74) *Attorney, Agent, or Firm* — Dicke, Billig & Czaja, PLLC

(57) ABSTRACT

A surgical cutting instrument including an outer tube having a bearing sleeve disposed within a lumen thereof, along with an inner wire assembly extending through the outer tube and the bearing sleeve. A cutting tip is connected to the inner wire assembly distal the outer tube. Conversely, a coupling chuck is connected to a proximal section of the inner wire assembly, with a housing maintaining the outer tube and the coupling chuck. When mounted to a motor, the inner wire assembly is rotated to effectuate a surgical cutting procedure at the cutting tip, with the bearing sleeve supporting the inner wire assembly relative to the outer tube during rotation.

20 Claims, 9 Drawing Sheets

(51) Int. Cl.
*A61B 17/00* (2006.01)
*A61B 17/29* (2006.01)

(52) U.S. Cl.
CPC ....... *A61B17/32002* (2013.01); *A61B 17/1662* (2013.01); *A61B 17/1679* (2013.01); *A61B 2017/00845* (2013.01); *A61B 2017/2904* (2013.01); *A61B 2017/320032* (2013.01)

(56) References Cited

U.S. PATENT DOCUMENTS

| | | |
|---|---|---|
| 4,811,736 A | 3/1989 | Griggs et al. |
| 5,222,956 A | 6/1993 | Waldron |
| 5,405,348 A | 4/1995 | Anspach, Jr. et al. |
| 5,976,165 A | 11/1999 | Ball et al. |
| 6,033,408 A | 3/2000 | Gage et al. |
| 6,456,524 B1 | 9/2002 | Perner et al. |
| 6,533,749 B1 * | 3/2003 | Mitusina et al. .......... 604/22 |
| 2003/0063823 A1 | 4/2003 | Del Rio et al. |
| 2003/0083681 A1 | 5/2003 | Moutafis et al. |
| 2005/0177168 A1 | 8/2005 | Brunnett et al. |

FOREIGN PATENT DOCUMENTS

| | | |
|---|---|---|
| EP | 1155776 | 11/2001 |
| FR | 1166884 | 6/1958 |
| GB | 2093353 | 9/1982 |
| JP | 01240615 | 9/1989 |
| JP | 09-108230 | 4/1997 |
| JP | 2003021213 | 1/2003 |
| RU | 2191898 | 5/2000 |
| WO | 03025102 | 3/2003 |
| WO | WO2005077284 | 8/2005 |

OTHER PUBLICATIONS

Bhushan, B.: "The Engineering Handbook," 1998, XP002351800; online at www.engnetbase.com; Chap. 21.3-21.5.

Kennedy, F.; Booser, E.; Wilcok, D.: "The Engineering Handbook," 1999; online at www.engnetbase.com; p. 3-129 to 3-133; p. 3-139 to 3-141.

\* cited by examiner

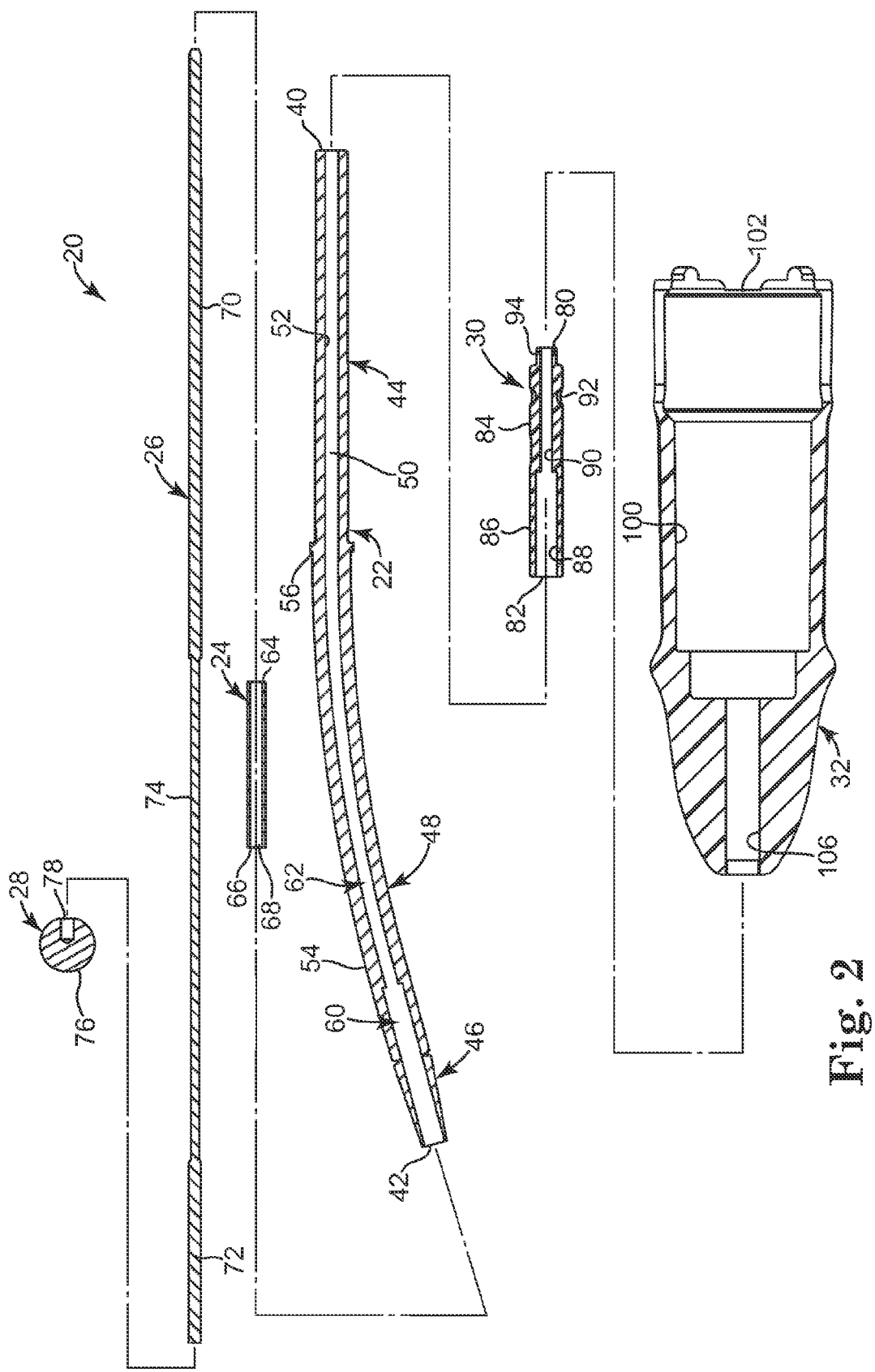

HIGH SPEED SURGICAL CUTTING INSTRUMENT

CROSS-REFERENCE TO RELATED APPLICATIONS

This application is a continuation of U.S. patent application Ser. No. 12/986,356, filed Jan. 7, 2011, entitled "HIGH SPEED SURGICAL INSTRUMENT", now U.S. Pat. No. 8,568,415, issued Oct. 29, 2013, which is a divisional of U.S. application Ser. No. 11/444,121, filed May 31, 2006, entitled "HIGH SPEED SURGICAL CUTTING INSTRUMENT", now U.S. Pat. No. 7,879,037, issued Feb. 1, 2011, which is a continuation-in-part of U.S. application Ser. No. 10/776,835, filed on Feb. 11, 2004, entitled "HIGH SPEED SURGICAL CUTTING INSTRUMENT", now U.S. Pat. No. 7,488,322, issued Feb. 10, 2009, the teachings of which are incorporated herein by reference.

BACKGROUND

The present invention relates to a surgical cutting instrument. More particularly, it relates to a high speed surgical cutting instruments, such as a bone-cutting bur, usable with various size cutting tips and adapted for minimal interference with surgical site visibility.

Surgical cutting instruments including a cutting tip are usually connected to a motorized handpiece for rotating the cutting tip at various speeds to perform a variety of surgical cutting procedures. Many high speed surgical cutting instrument designs impair visibility of a surgical site during a cutting procedure. For example, high speed surgical cutting instruments often employ a straight bur extender including a ball bearing assembly between an outer support sleeve and a rotating inner cutter shaft. Outer diameters of such outer support sleeves are relatively large (e.g., on the order of 6 mm) to accommodate a ball bearing assembly. Such relatively large outer diameters create blind spots and otherwise impair surgical site visibility during cutting. Other line-of-sight and handling concerns are often encountered with straight bur extenders. For example, the straight support sleeves associated with straight bur extenders are typically in or near a surgeon's line of sight during cutting.

In view of the above, it would be desirable for a surgical cutting instrument to have a reduced diameter and/or angle or bend away from an associated handpiece to improve visibility, ergonomics, or other performance or cost factors. Additionally, it would be desirable to provide a curved bur extender operable at relatively high speeds with small burs (e.g., about 2 mm) as well as larger burs (e.g., burs having diameters greater than about 2 mm, from about 3 mm to about 4 mm, or at least about 3 mm).

SUMMARY

Some aspects in accordance with principles of the present invention relate to a surgical cutting instrument for use with a motor having a drive mechanism. The surgical cutting instrument includes an outer tube, a bearing sleeve, an inner wire assembly, a cutting tip, a coupling chuck, and a housing. The outer tube defines a proximal region terminating at a proximal end, a distal region terminating at a distal end, and a lumen extending from the proximal end to the distal end. The bearing sleeve is substantially tubular in shape, and defines a proximal terminus, a distal terminus, and an inner passage. At least a portion of the bearing sleeve is secured within the lumen of the outer tube. The inner wire assembly defines a proximal section and a distal section, and extends through the lumen of the outer tube and through the inner passage of the bearing sleeve. The cutting tip is connected to the distal section of the inner wire assembly. Conversely, the coupling chuck is connected to the proximal section of the inner wire assembly and is adapted for connection to a drive mechanism of a motor. Finally, the housing maintains the proximal region of the outer tube and the coupling chuck, and is adapted for connection to a motor. With this configuration, the bearing sleeve supports the inner wire assembly upon rotation thereof relative to the outer tube during a cutting operation. In some embodiments, the cutting tip has a relatively large outer dimension (e.g., on the order of at least 3 mm), with the bearing sleeve minimizing vibration of the cutting tip.

Other aspects in accordance with principles of the present invention relate to a method of performing a surgical drilling procedure on bodily material at a target site of the patient. The method includes providing a surgical cutting instrument as described above. The bodily material at the target site is exposed, and the cutting tip is deployed against the bodily material. The inner wire assembly is rotated within the outer tube and the bearing sleeve to initiate a cutting interface between the cutting tip and the bodily material in contact therewith. In this regard, the distal section of the inner wire assembly is maintained by the bearing sleeve, and the proximal section of the inner wire assembly is maintained by the outer tube during rotation thereof. In some embodiments, the inner wire assembly is rotated at speeds of at least about 50,000 RPM. In other embodiments, the methodology is performed as part of an acoustic neuroma surgery.

BRIEF DESCRIPTION OF THE DRAWINGS

FIG. 2 is an exploded, cross-sectional view of the surgical cutting instrument of FIG. 1 in an unassembled form.

DETAILED DESCRIPTION

Figure 1:
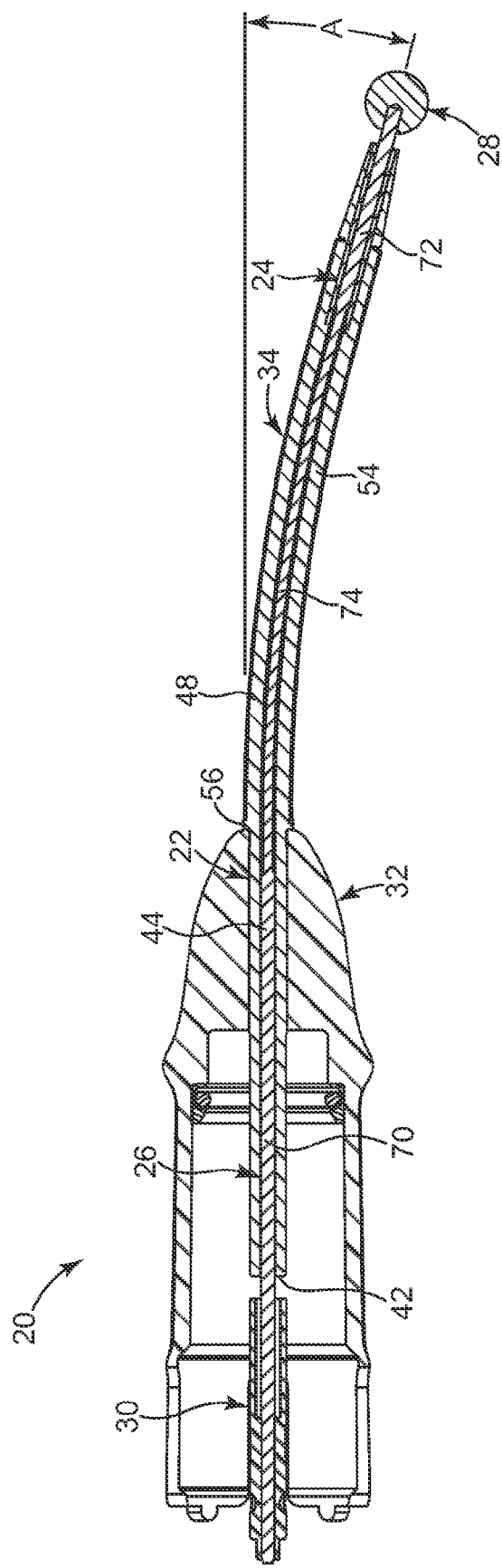
FIG. 1 is a cross-sectional view of a surgical cutting instrument in accordance with principles of the present invention.

Embodiments of high speed surgical cutting instruments in accordance with the present invention are to be understood cumulatively, as a whole, with features and principles of operation treated interchangeably as desired. With this in mind, a surgical cutting instrument 20 in accordance with principles of the present invention is shown in FIG. 1. The surgical cutting instrument 20 includes an outer support tube 22, a bearing sleeve 24, an inner wire assembly 26, a cutting tip 28, a coupling chuck 30, a housing 32, and an evaporative cooling sleeve 34. In general terms, the evaporative cooling sleeve 34 is secured over a portion of the outer tube 22. The bearing sleeve 24 is secured in the outer tube 22 with portions of the inner wire assembly 26 coaxially disposed within the bearing sleeve 24 and the outer tube 22, respectively.

The cutting tip 28 is connected to, and extends distally from, the inner wire assembly 26. The coupling chuck 30 is secured to the inner wire assembly 26 and is adapted for connection to a drive mechanism (not shown) of a motor (not shown). The housing 32 maintains the outer tube 22 and the coupling chuck 30, and is also adapted for connection to a motor.

As will be described in greater detail, some embodiments include the bearing sleeve 24 maintaining a portion of the inner wire assembly 26 and journal bearing being established between a portion of the inner wire assembly 26 and the bearing sleeve 24 upon rotation of the inner wire assembly 26 relative to the bearing sleeve 24. A journal bearing is also optionally established between a portion of the outer tube 22 and the inner wire assembly 26 upon rotation of the inner wire assembly 26 relative to the outer tube 22. As described in greater detail below, the instrument 20 and components thereof optionally provide one or more features that facilitate extremely high rotational speeds (e.g., including at least about 50,000 RPM and on the order of about 80,000 RPM) of a relatively large cutting tip 28 in the form of a bur, including, for example bur cutting tips having an outer diameter greater than about 2 mm, from about 3 mm to about 4 mm, or at least about 3 mm. Additionally, the outer tube 22 and the inner wire assembly 26 define one or more curved segments as desired.

FIG. 2 illustrates the surgical cutting instrument 20 in an unassembled state from an exploded, cross-sectional view. With reference to FIG. 2, the outer tube 22 is substantially elongate and tubular in shape. The outer tube 22 defines a proximal end 40, a distal end 42, a proximal region 44 terminating at the proximal end 40, and a distal region 46 terminating at the distal end 42. The outer tube 22 also includes an intermediate region 48 extending between the proximal and distal regions 44, 46. The outer tube 22 defines one or more inner diameters with a lumen 50 extending from the proximal end 40 to the distal end 42 at an inner surface 52 of the outer tube 22.

The outer tube 22 assumes a variety of longitudinal shapes as desired. For example, the outer tube 22 optionally defines a curved profile at or along one or both of the intermediate region 48 and the distal region 46. In some embodiments with a curved or bent profile, the distal region 46 is angularly offset from the proximal region 44. For example, the outer tube 22 extends through a radius of curvature from about 3 inches (about 76 mm) to about 6 inches (about 152 mm), although other dimensions are contemplated. In addition, the outer tube 22 is optionally constructed to facilitate formation of a rotating journal bearing (i.e., frictional sliding journal bearing) relative to the inner wire assembly 26 in a straight configuration or in conjunction with a curved configuration.

The proximal region 44 of the outer tube 22 is adapted to be received in the housing 32. Some embodiments include the proximal region 44 being substantially straight and uniform in outer diameter. For example, the outer diameter of the proximal region 44 is about 0.090 inch (about 2.3 mm), although other dimensions, such as tapers or other features are also contemplated.

The intermediate region 48 of the outer tube 22 can form a shoulder 56 that abuts the housing 32 upon final assembly. Some embodiments include a remainder of the intermediate region 48 extending distal the housing 32 upon final assembly) at a uniform outer diameter of about 0.110 inch (about 2.79 mm), including at a curved segment 54 and one or more straight segments, if desired.

The distal region 46 optionally tapers in outer diameter to the distal end 42. For example, the outer tube 22 tapers from an outer diameter of about 0.110 inch (about 2.79 mm) to a diameter of about 0.72 inch (about 18.3 mm) at the distal end 42, although other dimensions are also acceptable. Alternatively, the distal end 42 can be substantially free of any tapers.

The outer tube 22 defines one or more inner diameters along the lumen 50. For example, the lumen 50 is optionally defined by two or more lengths having different diameters. In the configuration of FIG. 2, the lumen 50 includes or is defined by a first segment 60 having a first diameter and a second segment 62 having a second diameter. However, as will be described in greater detail, some embodiments include the lumen 50 varying in diameter over three or more segments if desired. Regardless, the first segment 60 originates at the distal end 42 and extends proximally along the distal region 46. The second segment 62 extends proximal from the first segment 60 through a remainder of the outer tube 22 to the proximal end 40. The first segment 60, including the first diameter, is adapted to receive at least a portion of the bearing sleeve 24, for example via a press fit. In some embodiments, the first segment 60 has a length in the range of 0.35-0.65 inch (about 8.9-16.5 mm), for example 0.47 inch (11.9 mm), and a diameter in the range of 0.04-0.08 inch (1.0-2.0 mm), for example 0.06 inch (1.5 mm); by way of reference, a diameter of the second segment 62 is in the range of 0.02-0.06 (0.51-1.5 mm), for example, 0.037 inch (0.94 mm). It will be understood, however, that other dimensions are also contemplated.

Where the inner wire assembly 26 is relatively small in outer diameter, the lumen 50 is relatively small in diameter. It should be understood that reducing diameter size of the lumen 50 facilitates reduction of an overall outer diameter of the outer tube 22 while retaining sufficient wall thickness to help ensure desired strength and rigidity of the outer tube 22. As previously alluded to, reducing the outer diameter of the outer tube 22 facilitates an ability of a surgeon or other operator to see a surgical cutting site during a cutting operation. For example, portions of the outer tube 22 extending distal to the housing 32 (including or excluding the shoulder 56) define, in some embodiments, a maximum outer diameter of no more than about 0.125 inch (about 3.18 mm), although other dimensions are contemplated. The outer tube 22 is optionally constructed of a material selected to provide the outer tube 22 with high strength, high stiffness characteristics while satisfying dimensional and curvature constraints. For example, the outer tube 22 is formed of conventional surgical instrument materials, such as stainless steel.

The inner surface 52 of the outer tube 22 can be highly polished to facilitate formation of a rotating journal bearing subsequently described in greater detail. More particularly, it has surprisingly been found that polishing the inner surface 52 of the outer tube 22 to a surface roughness of not greater than 20µ inch, and in some embodiments, not greater than 10µ inch, facilitates viability of the surgical cutting instrument 20 incorporating the curvature and dimensional characteristics at high operational speeds. However, other embodiments include the inner surface 52 being relatively less polished or unpolished.

The bearing sleeve 24 can be an elongate, tubular body defining a proximal terminus 64, a distal terminus 66, and an inner passage 68 extending from the proximal terminus 64 to the distal terminus 66. With this construction, the bearing sleeve 24 forms or provides a bearing surface along the inner passage 68. Additionally, the bearing sleeve 24 is adapted to be inserted into the outer tube lumen 50 at the distal end 42 of the outer tube 22 (e.g., within the first segment 60 of the lumen 50). For example, the bearing sleeve 24 is optionally sized to be press fit, or otherwise define an interference fit, within the outer tube lumen 50 at the distal end 42. The inner passage 68 is shown generally as extending for a substantially continuous diameter; however, it should be understood that other features, for example stepped diameters or other selected variations in the inner passage diameter, are also contemplated.

Figure 3A:
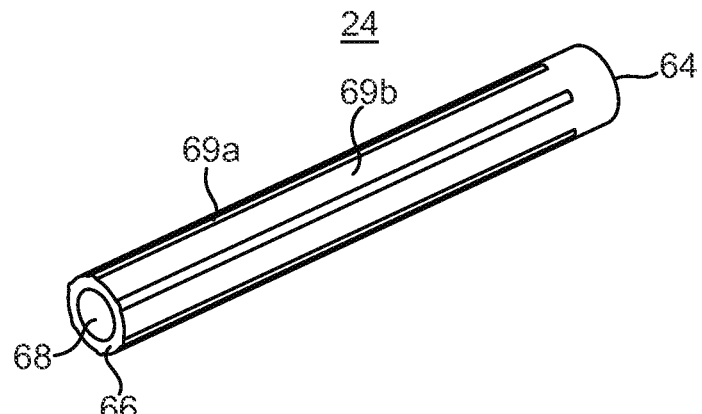
FIG. 3A is a perspective view of a bearing sleeve portion of the cutting instrument of FIG. 1.
Figure 3B:
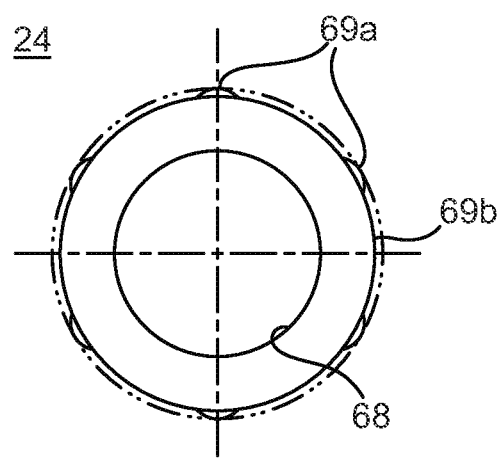
FIG. 3B is an end view of the bearing sleeve of FIG. 3A.

The bearing sleeve 24 is substantially cylindrical and circular in transverse cross-section, though other shapes, such as ellipsoid, for example, are also contemplated. In some embodiments, the bearing sleeve 24 has a length in the range of about 0.25-0.65 inch (about 6.35-16.5 mm), for example, 0.46 inch (11.7 mm); and an inner diameter in the range of about 0.02-0.06 inch (0.51-1.5 mm), for example 0.038 inch (0.97 mm); although other dimensions are contemplated. An outer diameter of the bearing sleeve 24 can be sized in accordance with the outer tube lumen 50 (e.g., at or along the first segment 60) so as to facilitate a press fit or interference fit. In this regard, and with reference to FIGS. 3A and 3B, the bearing sleeve 24 can include a plurality of longitudinal ribs 69a projecting from an exterior surface 69b. The ribs 69a combine to define an effective outer diameter approximating or slightly larger than the corresponding diameter of the outer tube lumen 50 (FIG. 2), for example in the range of 0.041-0.081 inch (1.04-2.06 mm), and can be 0.061 inch (1.55 mm). The bearing sleeve 24 outer diameter at the exterior surface 69b is slightly less than the effective outer diameter defined by the ribs 69a (e.g., on the order of 0.001-0.01 inch (0.025-0.25 mm) less). The circumferential spacing between the ribs 69a facilitates ease of press-fit assembly into the outer tube lumen 50 as the ribs 69a can more easily deform to account for tolerance variations. The ease of assembly can be further enhanced by the ribs 69a terminating distal the proximal terminus 64 (that is otherwise initially inserted into the outer tube lumen 50 during assembly). Further, upon final assembly, a slight air gap is established between the inner surface 52 (FIG. 2) of the outer tube 22 and the exterior surface 69b of the bearing sleeve 24, with this air gap assisting in cooling during use. Alternatively, the ribs 69a can be eliminated.

The bearing sleeve 24 can be formed from a variety of materials compatible with high speed rotation of the inner wire assembly 26, selected to exhibit low wear and low temperature characteristics in the presence of the rotating wire assembly 26. To this end, a material of the bearing sleeve 24 is, in some embodiments, selected to be a low wear material that will not generate adverse debris (e.g., black in color) when subjected to a high speed rotation of the otherwise metallic inner wire assembly 26, and thus is in one embodiment formed from a material other than metal. For example, the bearing sleeve 24 is formed of a material including one or more of the following: polyetheretherketone (PEEK); PEEK with carbon additives; PEEK with polytetrafluoroethylene (PTFE) and carbon additives; PTFE, including PTFE with various additives; ceramics, such as sapphire, for example. In other embodiments, the bearing sleeve 24 can be formed of a surgically-safe metal.

Returning to FIG. 2, the inner wire assembly 26 includes a proximal section 70, a distal section 72, and an intermediate section 74, the intermediate section 74 between the proximal section 70 and the distal section 72. In some embodiments, the inner wire assembly 26 has an overall longitudinal length greater than that of the outer tube 22 such that upon final assembly, the proximal and distal sections 70, 72 extend from the proximal and distal ends 40, 42, respectively, of the outer tube 22.

The proximal section 70 is generally adapted to be connected to the coupling chuck 30, as will be subsequently described in greater detail. In turn, the distal section 72 is adapted to be connected to the cutting tip 28, as will also be described in greater detail. The intermediate section 74 is generally adapted to provide a flexible, mechanical connection between the proximal and distal sections 70, 72 such that rotation of the proximal section 70 translates to rotation of the distal section 72, and thus, the cutting tip 28. Some embodiments include forming the intermediate section 74 to define a length at least as long as an extension of the curved section 54 of the outer tube 22. For example, the intermediate section 74 is optionally formed to have a margin at each end, such that the intermediate section 74 is somewhat longer than the curved section 54 or curved sections where appropriate. Such "over sizing" of the intermediate section 74 optionally helps ensure that the inner wire assembly 26 does not bind with the outer tube 22, for example.

As previously alluded to, the intermediate section 74 can be more flexible than at least one of the proximal section 70 and the distal section 72. For example, the intermediate section 74 optionally defines a substantially smaller diameter than one or both of the proximal section 70 and the distal section 72 in order to provide relatively more flexibility to the intermediate section 74, for example. The diameter of the intermediate section 70 can be selected to be smaller than that of the proximal section 70 and the distal section 72, in part, because the intermediate section 74 does not support bending loads induced by the cutting tip 28 to the same extent as the distal section 72. Additionally, or alternatively, the intermediate section 74 is formed of more flexible materials than one or both of the proximal section 70 and the distal section 72 or includes other features to promote flexibility. By way of non-limiting examples, the diameter of the proximal and distal sections 70, 72 is in the range of about 0.025-0.045 inch (0.635-1.14 mm), for example 0.035 inch (0.89 mm); whereas the diameter of the intermediate section 74 can be in the range of about 0.015-0.035 inch (0.38-0.89 mm), for example 0.024 inch (0.61 mm), it being understood that a variety or other dimensions are also contemplated. For example, in alternative embodiments, the inner wire assembly 26 has a uniform diameter.

The inner wire assembly 26 is optionally adapted to facilitate establishment of a rotating journal bearing relative to the outer tube 22 and the bearing sleeve 24. In some embodiments, the additional flexibility of the intermediate section 74 facilitates rotation of the intermediate section 74 within the outer tube 22 at the curved section 54. For example, flexibility of the intermediate section 74 has the potential to reduce fatigue effects on the inner wire assembly 26, binding of the inner wire assembly 26 within the outer tube 22, for example proximate the curved segment 54, and/or overall resistance to rotation of the inner wire assembly 26 while in a bent configuration. A relatively larger diameter, and therefore rigidity, of the proximal section 70 optionally provides additional structural support for connection to the coupling chuck 30, as well as a more stable journal bearing within the outer tube 22. Additionally, a relatively larger diameter of the distal section 72 provides additional structural support for the cutting tip 28 (e.g., when subjected to bending loads and/or impact chatter loads during cutting), as well as a more stable journal bearing within the bearing sleeve 24 as desired.

Diametric clearances between the outer tube lumen 50 and the inner wire assembly 26, and bearing sleeve inner passage 68 and the inner wire assembly 26, are optionally selected to promote reduced potential for binding and establishment of effective journal bearings. For example, the outer diameter of the proximal section 70 of the inner wire assembly 26 can be about 0.001-0.005 inch (0.025-0.127 mm), for example 0.002 inch (0.05 mm) less than the diameter of the second segment 62 of the outer tube lumen 50. In turn, the outer diameter of the distal section 72 of the inner wire assembly 26 can be about 0.001-0.005 inch (0.025-0.127 mm), for example 0.002 inch (0.05 mm), less than the diameter of the inner passage 68 of the bearing sleeve 24. Conversely, the outer diameter of the intermediate section 74 can be about 0.005-0.025 inch (0.127-0.635 mm), for example 0.013 inch (0.33 mm), less than the diameter of the second segment 62 of the outer tube lumen 50, for example. It will be understood, however, that other dimensions are also contemplated.

As alluded to above, the inner wire assembly 26 is generally formed to exhibit high strength and good fatigue characteristics. Fatigue strength is a function of material selection and end geometry, as well as other variables. In some embodiments, the inner wire assembly 26 is formed to exhibit a fatigue strength or endurance limit of at least about 75 Kpsi where the outer tube 22 imparts a curve onto a longitudinal length of the inner wire assembly 26. It has surprisingly been found that such fatigue strength characteristics and dimensions are optionally achieved with an appropriate tool steel material, such as M-series tool steels (molybdenum high speed tool steels), A-series tool steels (medium-alloy air-hardening cold work tool steels), and others.

For example, the inner wire assembly 26 can be a homogenous, one-piece wire M2 tool steel. Alternative other materials exhibiting the desired durability and fracture resistance are employed for the inner wire assembly 26, including, for example, other tool steels; 304V high tensile strength drawn wire; other steel wire materials subjected to a roll burnishing process that improves the fatigue strength of the wire by putting the outer surface into a state of compression; other steel wire materials subjected to ultrasonic shot peening or laser shot peening for improving fatigue strength of the wire by putting the outer surface into a state of compression; and others. Even further, in some embodiments other non-steel metals such as iridium, osmium, or ruthenium are optionally employed, as are ceramics such as silicon carbide, silicon nitride, boron carbide, titanium carbide, tungsten carbide, and others. Conventional materials that do not otherwise conform to the above-described strength and stiffness parameters can also be employed.

To further enhance wear resistance properties of the inner wire assembly 26, the inner wire assembly 26 can be subjected to processing (e.g., heat treated) and/or coated with additional material(s), resulting in a Rockwell Hardness of not less than 50 HRC or not less than about 60 HRC, for example, although other characteristic Rockwell Hardness values are also contemplated. Some embodiments include employing a hardened material (not shown) coating to provide a dense carbon finish to the inner wire assembly 26. For example, the hardened material coating can be a dense carbon (diamond-like coating), coated to a thickness of not more than about 0.3 mm, although other dimensions are contemplated. Other coating materials are also optionally employed, such as, for example, zirconium nitride, chrome, polytetrafluoroethylene (PTFE) or other fluorocarbon materials, titanium nitride, electroless nickel impregnated with PTFE, and others.

The cutting tip 28 can assume a variety of forms and generally includes a cutting bur 76 and an attachment end 78 adapted for connection to the distal section 72 of the inner wire assembly 26. The attachment end 78 can be configured to coaxially receive the distal section 72 of the inner wire assembly 26. Regardless, the inner wire assembly 26 is can be connected to attachment end 78 via a number of known processes such as, for example, laser welding, brazing, press fitting, thermal shrink fitting, adhesive, and others. Alternatively, the attachment end 78 of the inner wire assembly 26 and the cutting tip 28 can be connected by integrally forming the distal section 72 of the inner wire assembly 26 and the cutting tip 28 (see, e.g., cutting instrument 120 of FIG. 5). For example, the inner wire assembly 26 and the cutting tip 28 are optionally machined from a single piece of stock material. The cutting bur 76 optionally defines an outer diameter of greater than about 2 mm, an outer diameter from about 3 mm to about 4 mm, or an outer diameter of about 3 mm or more, for example, although other dimensions are contemplated. In particular, the cutting bur 76 optionally assumes a variety of shapes and sizes known in the art (e.g., 3 mm fluted, 4 mm diamond and others).

The coupling chuck 30 is generally configured to facilitate connection of the motor drive mechanism (not shown) to the inner wire assembly 26. As a point of reference, each of the motor (not shown) and the drive mechanism assumes a variety of forms as desired. For example, the motor is optionally of a type typically employed with surgical cutting instruments, such as electric, battery powered or pneumatic. Also, any other type of motor or drill drive system is employed as desired. Similarly, the drive mechanism is optionally of a type typically employed with surgical cutting instruments that facilitate connection or coupling to the cutting device, such as mechanical connection, a non-contacting magnetic connection, a non-contacting air driven coupling (e.g., an air vane), and others. With this in mind, the coupling chuck 30 is adapted for use with a mechanical-type drive mechanism, it being understood that the coupling chuck 30 is can be configured in accordance with any other type of drive mechanism.

The coupling chuck 30 defines a proximal end 80, a distal end 82, a proximal portion 84 extending to the proximal end 80, and a distal portion 86 extending to the distal end 82. The distal portion 86 forms a first passage 88 originating at the distal end 82. The first passage 88 is sized to receive the proximal section 70 of the inner wire assembly 26. The proximal portion 84 can further form a second passage 90 extending proximally from the first passage 88 to the proximal end 80. The second passage 90 is sized to coaxially receive and maintain the proximal section 70 of the inner wire assembly 26. Alternatively, (see, e.g., surgical cutting instrument 320 of FIG. 8A), the second passage 90 can terminate distal the proximal end 80 of the coupling chuck 30 as a closed, blind hole.

Some embodiments include the proximal portion 84 forming a groove 92 and a tang 94 each adapted to facilitate coupling to the drill motor drive shaft (not shown). The tang 94 is of a reduced diameter, and serves as a guide surface that promotes rapid, consistent assembly of the drive mechanism to the coupling chuck 30. However, the coupling chuck 30 assume a variety of other configurations, and assembly of the coupling chuck 30 to the outer tube 22 and/or the inner wire assembly 26 is also optionally varied as desired. For example, the coupling chuck 30 can be an integrally formed part of the inner wire assembly 26.

Similarly to the coupling chuck 30, the housing 32 can assume a variety of forms and is generally configured to support the outer tube 22 as well as facilitate connection of the coupling chuck 30, and thus the inner wire assembly 26, to a motor (not shown). The housing 32 can form a central aperture 100 having an open proximal end 102. The central aperture 100 is sized to receive at least a portion of the motor. The housing 32 is configured to facilitate attachment to the drill motor via snap fit, threads, interference fit, and others. The housing 32 defines a passage 106 fluidly connected to the aperture 100. The passage 106 is sized to maintain the outer tube 22, and can be formed during an insert molding procedure or otherwise. For example, the housing 32 is optionally insert molded over the outer tube 22. Also, a variety of other assembly techniques for connecting the outer tube 22 and the housing 32 can be employed, such as gluing, welding, press-fitting, thermal shrink fitting, and others.

In some embodiments, the evaporative cooling sleeve 34 (FIG. 1) is provided and is secured or formed over an exterior of the outer tube 22 and extends from the proximal the housing 32 to the distal region 46. The cooling sleeve 34 is formed of a variety of materials, for example fabric material such as nylon, silk, polypropylene, polyester, cotton, and others. In particular, the cooling sleeve 34 is optionally uncoated nylon. Regardless, the cooling sleeve 34 can readily conform to any curved segment(s) defined by the outer tube 22. For example, the cooling sleeve 34 is constructed as a braided tube or a coil of thread wound directly onto the outer tube 22. The cooling sleeve 34 is optionally secured over the outer tube 22 via a variety of means. For example, opposing ends of the cooling sleeve 34 are secured to the outer tube 22 by clamping or adhesive as desired. The cooling sleeve 34 is generally constructed to absorb fluids (e.g., bodily fluids at a surgical site, irrigation fluids delivered during a surgical procedure, and others) and in operation wicks absorbed fluids toward the housing 32. In other words, fluids absorbed by the cooling sleeve 34, for example proximate the distal end 42 of the outer tube 22, are conducted proximally by the cooling sleeve 34 toward the proximal region 44 of the outer tube 22 until a substantial portion or an entirety of the cooling sleeve 34 is saturated. While the cooling sleeve 34 is shown in FIG. 1 as extending along a substantial length of the outer tube 22, the cooling sleeve 34 need not extend to the housing 32. Further, the cooling sleeve 34 can be constructed and sized to encompass an entirety of the outer tube 22.

During use, fluids absorbed by the cooling sleeve 34 evaporate via heat generated by rotation of the inner wire assembly 26 (FIG. 1) relative to the outer tube 22, serving to cool the outer tube 22. With this construction, as the outer tube 22 conducts more heat, the evaporative process facilitated by the cooling sleeve 34 becomes more aggressive, regulating a surface temperature of the outer tube 22 to a relatively consistent level, for example. In operation, it has been surprisingly found that regardless of a temperature of the outer tube 22, the cooling sleeve 34 serves to cool the outer tube 22 to a substantially nominal temperature (within 10° C.), in the presence of fluids. Regardless, an enhanced cooling effect is provided in conjunction with fluids proximate the surgical site. Alternatively, however, the cooling sleeve 34 can be eliminated.

With respect to assembly of the outer tube 22 and the inner wire assembly 26, a lubricant (not shown) is optionally provided in the outer tube lumen 50 along a length of an interface between the inner wire assembly 26 and the outer tube 22. The lubricant can facilitate formation of a hydrodynamic journal bearing between the outer tube 22 and the inner wire assembly 26. In particular, the inner wire assembly 26 is supported by a hydrodynamic effect and effectively "floats" relative to the outer tube 22 upon rotation of the inner wire assembly 26 as desired. Lubricant is also optionally disposed in the bearing sleeve inner passage 68 along a length of an interface between the inner wire assembly 26 and the bearing sleeve 24 to provide a substantially similar hydrodynamic effect between the bearing sleeve 24 and the inner wire assembly 26 as desired.

With this in mind, the lubricant can be a grease lubricant. The lubricant can exhibit a dynamic viscosity of at least about 100 mm$^2$/s at 40° C.; or from about 150 mm$^2$/s at 40° C. to about 250 mm$^2$/s at 40° C., and is hydrophobic in nature. One acceptable grease lubricant is a synthetic hydrocarbon material thickened with silica available, for example, from Nye Lubricants, Inc., of Fairhaven, Mass., under the trade name "Nye NYOGEL® 670." Also, other lubricant materials, such as commercially available greases, can be employed as desired. Alternatively, the lubricant can be eliminated.

Figure 4:
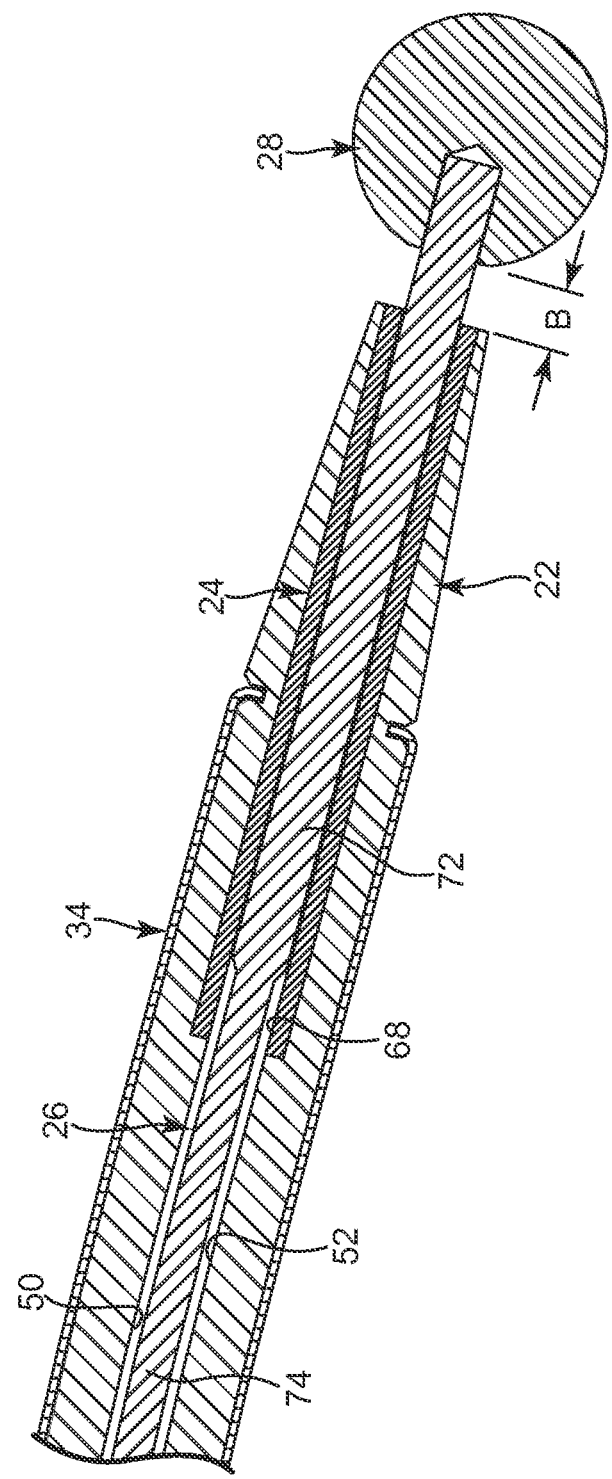
FIG. 4 is an enlarged cross-sectional view of the surgical cutting instrument of FIG. 1.

With reference to FIG. 4, assembly of the surgical cutting instrument 20 toward the distal end 42 of the outer tube 22 can be described in greater detail. The surgical cutting instrument 20 is assembled by coaxially disposing the bearing sleeve 24 in the outer tube lumen 50. For example, the bearing sleeve 24 is optionally press fit or defines an interference fit with the outer tube 22. The bearing sleeve 24 is secured in the outer tube lumen 50 (e.g., at the first segment 60 best shown in FIG. 2) such that the bearing sleeve 24 and the outer tube 22 are substantially rotationally fixed relative to one another. Additionally, the bearing sleeve 24 can be entirely received in the lumen 50. For example, the bearing sleeve 24 can have substantially the same length as the first segment 60 of the lumen 50 such that when the bearing sleeve 24 is inserted into the outer tube lumen 50, the distal terminus 66 of the bearing sleeve 24 and the distal end 42 of the outer tube 22 are substantially coterminous. Further, some embodiments include the inner passage 68 and the second segment 62 of the lumen 50 defining substantially the same diameter, such that there is a substantially continuous effective inner diameter from the inner passage 68 of the bearing sleeve 24 to the lumen 50 of the outer tube 22 at the second segment 62 of the lumen 50. Alternatively, a stepped-diameter transition, for example, is also contemplated (see, e.g., surgical cutting instrument 120 of FIG. 5).

With reference to FIG. 1, the inner wire assembly 26 is generally disposed within the lumen 50 (FIG. 2) of the outer tube 22. As previously described, a lubricant (not shown), such as a grease lubricant, can optionally be disposed along at least a portion or an entirety of the interface between the inner wire assembly 26 and the inner surface 52 (FIG. 2) of the outer tube 22, as well as between the interface between the bearing sleeve 24 and the inner wire assembly 26. With configurations in which the outer tube 22 includes or forms at least one curved segment 54, upon placement of the inner wire assembly 26 within the outer tube 22, the inner wire assembly 26 assumes a shape of the outer tube 22, and thus, the curved segment 54. With this in mind, the outer tube 22/inner wire assembly 26 can assume a variety of longitudinal shapes including one or more curved segments (for example, at the curved segment 54) and one or more straight segments.

With reference to FIG. 4, at least a portion of the distal section 72 of the inner wire assembly 26 is optionally disposed in the inner passage 68 of the bearing sleeve 24 and extends distally from the outer tube 22 and the bearing sleeve 24. The distal section 72 of the inner wire assembly 26 can be maintained by the bearing sleeve 24 such that the distal section 72 of the inner wire assembly 26 does not contact the inner surface 52 of the outer tube 22 upon rotation of the inner wire assembly 26 and/or while the inner wire assembly 26 is stationary. Thus, the bearing sleeve 24 serves to maintain the distal section 72 of inner wire assembly 26 such that any contact (incidental or intentional) is at the interface between the bearing sleeve 24 and the distal section 72, rather than contact between the outer tube 22 and the distal section 72.

In some embodiments, the distal section 72 of the inner wire assembly 26 is supported by the bearing sleeve 24 in a substantially linear configuration that is free of overt bends or curves. As alluded to above, the distal section 72 of the inner wire assembly 26 is optionally substantially thicker in diameter than the intermediate section 74, such that the distal section 72 is more structurally rigid than the intermediate section 74, and thus more suited to rotation within a substantially linear, or straight, portion of the outer tube 22.

Increasing the diameter of the distal section 72 of the inner wire assembly 26 and/or use of the bearing sleeve 24 serves several purposes. For example, increasing a thickness of the distal section 72 can increase rigidity of the assembly proximate the cutting tip 28. Thus, the assembly includes greater resistance to bending forces encountered at the cutting tip 28 during a cutting operation as desired. Also, adding rigidity is often particularly advantageous as cutting tip size increases (e.g., cutting burs of greater than about 2 mm, cutting burs from about 3 mm to about 4 mm, or cutting burs at least about 4 mm). With increased mass and/or size, inertial forces are potentially increased at the cutting tip 28, resulting in a potential for greater vibration or other undesirable transverse movement at the cutting tip 28. Such undesirable movement often results in more difficult cutting operations, increased fatiguing of the inner wire assembly 26, increased debris, increased temperatures, or other factors reducing cutting operation efficacy in general. Further, where the selected cutting tip 28 has an increased size, chatter loads on the cutting tip 28 will also increase, which in turn increases the bending stress and impact loads on the distal section 72 of the inner wire assembly 26. The increased diameter of the distal section 72, in accordance with some embodiments, reduces the stress to more acceptable levels.

According to the examples of undesirable effects described above, vibration or movement makes it more difficult to accurately cut along a desired cutting path without unwanted deviations. Additionally, vibrations and increased bending due to transverse movement from inertial effects, including increases in both periodicity and degree of bend, result in greater component fatigue. Undesirable movement at the cutting tip 28 also potentially increases debris generation; for example, increased transverse movement at the cutting tip 28 translates into increased transverse movement of the inner wire assembly 26 within the outer tube 22, thereby increasing contact and/or contact forces between the inner wire assembly 26 and the inner surface 52 of the outer tube 22 and/or the inner surface of the bearing sleeve 24. Furthermore, such vibration and added contact can also result in an undesirable increase in temperature due to frictional effects.

With the above in mind, the bearing sleeve 24 is adapted to reduce undesirable vibrational movement at the tip 28, for example by serving as a vibrational dampener. In particular, the bearing sleeve 24 is optionally formed of a vibrational dampening material, such as a relatively softer material than a material of the distal region 46 of the outer tube 22. Debris from the outer tube 22 and/or inner wire assembly 26 are also reduced via use of the bearing sleeve 24. For example, with configurations in which the distal section 72 and the outer tube 22 come into contact, the potential for debris comprising particles of the outer tube 22 and/or distal section 72 of the inner wire assembly 26 exists. However, where the bearing sleeve 24 is used to maintain the distal section 72 of the inner wire assembly 26, overall debris from the outer tube 22 and/or inner wire assembly 26 can be reduced, for example by forming the bearing sleeve 24 of a relatively soft material in comparison to the inner wire assembly 26, such as PEEK materials, for example. Such relatively softer, or more forgiving, materials can be used to reduce abrasion and/or impact forces from transverse movement at the distal section 72 of the inner wire assembly 26.

In some embodiments, design features of the surgical cutting instrument 20, such as material selection and the resultant journal bearing, allow for limited exposure of the inner wire assembly 26 distal the distal end 42 of the outer tube 22, represented at B in FIG. 4. For example, the exposed length B of the inner wire assembly 26 is not greater than about 0.1 inch (about 2.54 mm); as another example, the exposed length B is not greater than about 0.05 inch (about 1.3 mm), it being understood that other dimensions are contemplated.

With reference to FIG. 1, upon assembly, the proximal section 70 of the inner wire assembly 26 is generally disposed in the proximal region 44 of the outer tube 22, and extends from the distal end 42 thereof. The outer tube lumen 50 (FIG. 3) at the proximal region 44 is, in one embodiment, substantially linear such that the proximal section 70 of the inner wire assembly 26 is supported in a linear configuration substantially free of bends or curves. As alluded to above, the proximal section 70 of the inner wire assembly 26 can be substantially thicker in diameter than the intermediate section 74, such that the proximal section 70 is more structurally rigid than the intermediate section 74, and thus more suited to rotation within a substantially linear, or straight, portion of the outer tube 22. A more structurally rigid design at the proximal section 70 is advantageous in many respects. For example, the proximal section 70 is can be more resistant to torsion, flexing, or bending when a rotational force is being imparted on the inner wire assembly 26 via the motor (not shown).

In turn, at least a portion of the intermediate section 74 of the inner wire assembly 26 can be disposed in the intermediate region 48 of the outer tube 22. For example, where the curved segment 54 of the outer tube 22 is located at the intermediate region 48, the intermediate section 74 of the inner wire assembly 26 extends through the curved segment 54 (or segments) and also takes on a curved shape. In particular, the intermediate section 74 is adapted to be rotated in the outer tube 22 while maintaining the curved shape. As previously described, the intermediate section 74 has a substantially smaller diameter than the proximal section 72 such that the intermediate section 74 defines a substantially greater diametric clearance with the outer tube 22 than a diametric clearance between the outer tube 22 and the proximal section 72. As a result, the potential for binding or unwanted interference between the inner wire assembly intermediate section 74 and the outer tube intermediate region 48, due to their respective curved shapes, for example, is reduced. Additionally, where provided, the smaller diameter of the intermediate section 74 can help to increase flexibility of the intermediate section 74, thereby also reducing the potential for binding or other unwanted interference between the outer tube 22 and the inner wire assembly 26.

The outer tube 22 is assembled to the housing 32 with the intermediate region 48 and the distal region 46 extending distal the housing 32. As previously described, the housing 32 can be insert molded over the outer tube 22, with the inner wire assembly 26 then being placed within the lumen 50. In some embodiments, the optional shoulder 56 of the intermediate region 48 provides a stop surface for positioning against the housing 32 if desired.

Figure 5:
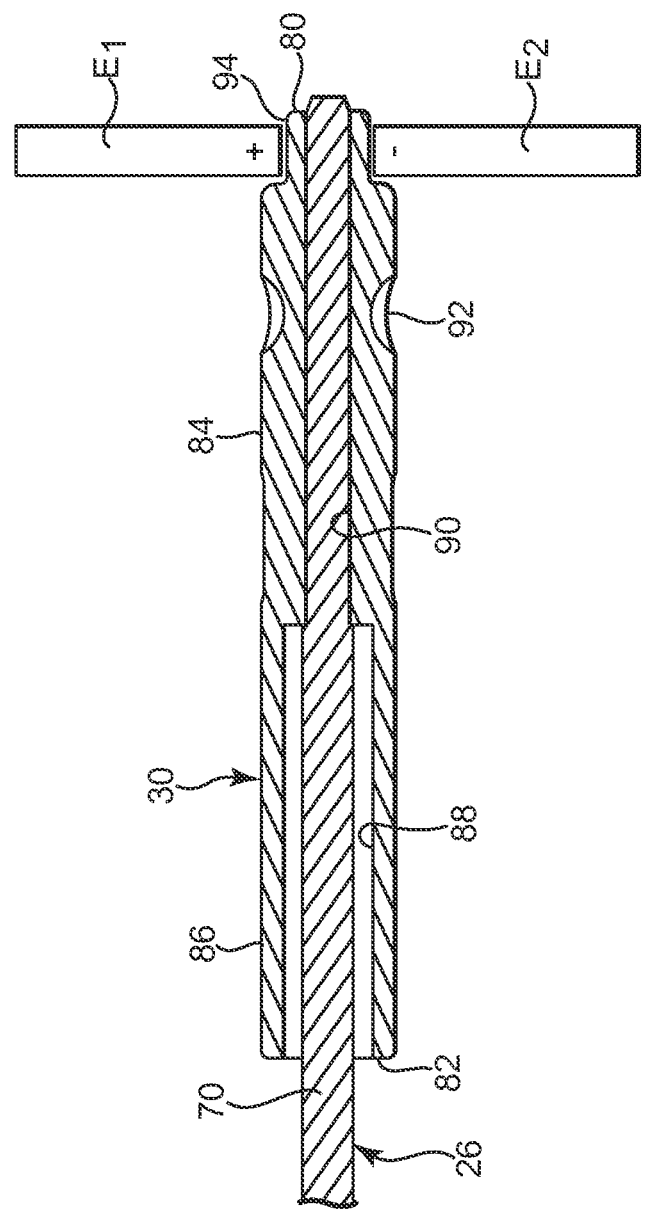
FIG. 5 is a schematic view illustrating a method of connecting an inner wire assembly to a coupling chuck of the surgical cutting instrument of FIG. 1.

With reference to FIG. 5, in some embodiments the coupling chuck 30 is secured to the proximal section 70 of the inner wire assembly 26 by resistance welding. In particular, a first electrode $E_1$ and a second electrode $E_2$ are optionally used to weld the inner wire assembly 26 to the coupling chuck 30 with a portion of the proximal section 70 protruding from, or also, substantially coterminous with, the proximal end 80 of the coupling chuck 30. The weld joint is created by applying voltage to the electrode $E_1$. A relatively large electrical current passes from the first electrode $E_1$, through the coupling chuck 30 and the proximal section 70 of the inner wire assembly 26, and to the second electrode $E_2$. The current heats the coupling chuck 30/inner wire assembly 26 to the point where the material between the electrodes $E_1$ and $E_2$ softens; upon cooling and hardening, a welded joint is formed. However, other methods of connecting the wire assembly 26 to the coupling chuck 30, such as via crimping, are also contemplated.

The manner of assembly using resistance welding is advantageous in many respects. For example, using crimping in the absence of resistance welding, the proximal section 70 of the inner wire assembly 26 defines opposing flats (not shown) that are aligned to crimping points of the coupling chuck 30 prior to crimping. Further, the second passage 90 is closed, or is otherwise a "blind hole." A user performing the crimping-type assembly ensures that the proximal section 70 is fully inserted into the second passage 90, ensures that the inner wire flats are aligned, or properly indexed, to the crimping points, then stakes, or secures, the coupling chuck 30 and the inner wire assembly 26 in that position, and ultimately uses a crimping tool or machine to crimp the coupling chuck 30 to the inner wire assembly 26. From this, it should be understood that more potential for user-induced inefficiencies exist. In particular, such methodology, including alignment steps, can be highly user dependent.

On the other hand, with resistance welding, the proximal section 70 of the inner wire assembly 26 is inserted into the second passage 90 of the coupling chuck 30 and extends proximally from the coupling chuck 30. In this manner, the user performing assembly is able to better ensure that the proximal section 70 has been properly inserted into the coupling chuck 30. Further, resistance welding forms a substantially stronger connection between the inner wire assembly 26 and the coupling chuck 30. In particular, an actual weld of material is formed, rather than generation of a mechanical interference, or crimp. However, crimping, resistance welding, or other methods of connecting the inner wire assembly 26 to the coupling chuck 30 are all within the scope of the present invention.

With reference to FIG. 4, the cutting tip 28 is attached to the distal section 72 of the inner wire assembly 26. The cutting tip 28 can be secured to the distal section 72 via a variety of means, including brazing, laser welding, adhesives, threads or screw means, and other means for connecting or fastening, including those already described above. Alternatively, the cutting tip 28 can be substantially continuously formed with the distal section 72 (see, e.g., surgical cutting instrument 120 of FIG. 6).

Returning to FIG. 1, during use, a motor (not shown) is connected to the housing 32, with the drive mechanism (not shown) connected to the coupling chuck 30. The motor is then operated to rotate the coupling chuck 30 and thus the inner wire assembly 26. Rotation of the inner wire assembly 26 relative to the outer tube 22 can create a rotating journal bearing between the inner wire assembly 26 and the inner surface 52 (FIG. 2) of the outer tube 22 along at least a portion of a length of the outer tube 22. For example, a journal bearing can be formed between the proximal section 70 of the inner wire assembly 26 and the proximal region 44 of the outer tube 22. Additionally, a journal bearing is optionally generated between the inner wire assembly 26 and the bearing sleeve 24. If desired, a journal bearing can also be formed between the intermediate section 74 of the inner wire assembly 26 and the outer tube 22.

Where provided, the lubricant, for example a grease lubricant, can generate a hydrodynamic journal bearing and/or combination rotating and hydrodynamic journal bearing between the inner wire assembly 26 and the inner surface 52 of the outer tube 22 upon rotation of the inner wire assembly 26. The lubricant also optionally forms a hydrodynamic journal bearing and/or combination rotating and hydrodynamic journal bearing between the inner wire assembly 26 and the bearing sleeve 24 upon rotation of the inner wire assembly 26. Regardless, some configurations include the surgical cutting instrument 20 being characterized by the absence of a ball bearing assembly between the outer tube 22 and the inner wire assembly 26.

The surgical cutting instrument 20 of the present invention is capable of maintaining its structural integrity at highly elevated rotational speeds. For example, the surgical cutting instrument 20 is operated at rotational speeds in excess of 50,000 RPM, such as about 80,000 RPM, as desired. Further, embodiments where the inner wire assembly 26 is formed of M2 tool steel, the inner surface 52 of the outer tube 22 is highly polished, and a grease lubricant is disposed between the inner wire assembly 26 and the inner surface 52 of the outer tube 22, have been surprisingly found to provide many advantages. For example, such configurations allow the outer tube 22/inner wire assembly 26 to include the curved segment 54 extending through a radius of curvature such that the proximal region 44 and the distal region 46 extend at an angular offset A of about 15°, for example, although other dimension are contemplated.

Thus, the resultant surgical cutting instrument 20 facilitate high-speed surgical cutting procedures with minimal interference to the surgeon's visibility via the small outer diameter and/or curved nature of the outer tube 22/inner wire assembly 26. The minimal heat generation renders the surgical cutting instrument 20 highly safe for virtually all surgical applications, as does the minimal exposed length B of the inner wire assembly 26. Further, the outer tube 22 is highly stiff, greatly promoting handling and use during a surgical procedure. The above-described performance attributes are optionally further improved with a hardened material coating (e.g., diamond-like coating) on the inner wire assembly 26. While each of the above-described features (e.g., material selections, processing, and lubricant selection) have a synergistic effect in producing a viable, high speed, low profile, curved surgical cutting instrument, variations on one or more of these features can be employed and remain within the scope of the present invention.

For example, an alternative surgical cutting instrument 120 in accordance with principles of the present invention is described with reference to FIG. 6. In general terms, the surgical cutting instrument 120 includes features and operates according to principles substantially similar to those described in association the surgical cutting instrument 20 (FIG. 1). With this in mind, the surgical cutting instrument 120 includes a support tube 122, a bearing sleeve 124, an inner wire assembly 126, a cutting tip 128, a coupling chuck 130, a housing 132, and an evaporative cooling sleeve 134. Similar to the surgical cutting instrument 20, the inner wire assembly 126 is coaxially disposed within a lumen 150 (FIG. 7) formed by the outer tube 122, with the outer tube 122 including at least one curved segment 154.

The outer tube 122 defines a proximal end 140, a distal end 142 (FIG. 7), a proximal region 144 terminating at the proximal end 140 and a distal region 146 terminating at the distal end 142. The outer tube 122 also includes an intermediate region 148 extending between the proximal and distal regions 144, 146. The outer tube 122 defines one or more inner diameters with the lumen 150 extending from the proximal end 140 to the distal end 142 of the outer tube 122.

The outer tube 122 can define a curved profile (e.g., the curved segment 154) at or along the intermediate region 148. With a curved or bent profile, the distal region 146 is angularly offset from the proximal region 144. As described in association with the surgical cutting instrument 20, the outer tube 22 is optionally constructed to facilitate formation of a rotating journal bearing (i.e., frictional sliding journal bearing) relative to the inner wire assembly 126 in conjunction with a curved construction. Alternatively, the outer tube 122 can be straight.

Figure 7:
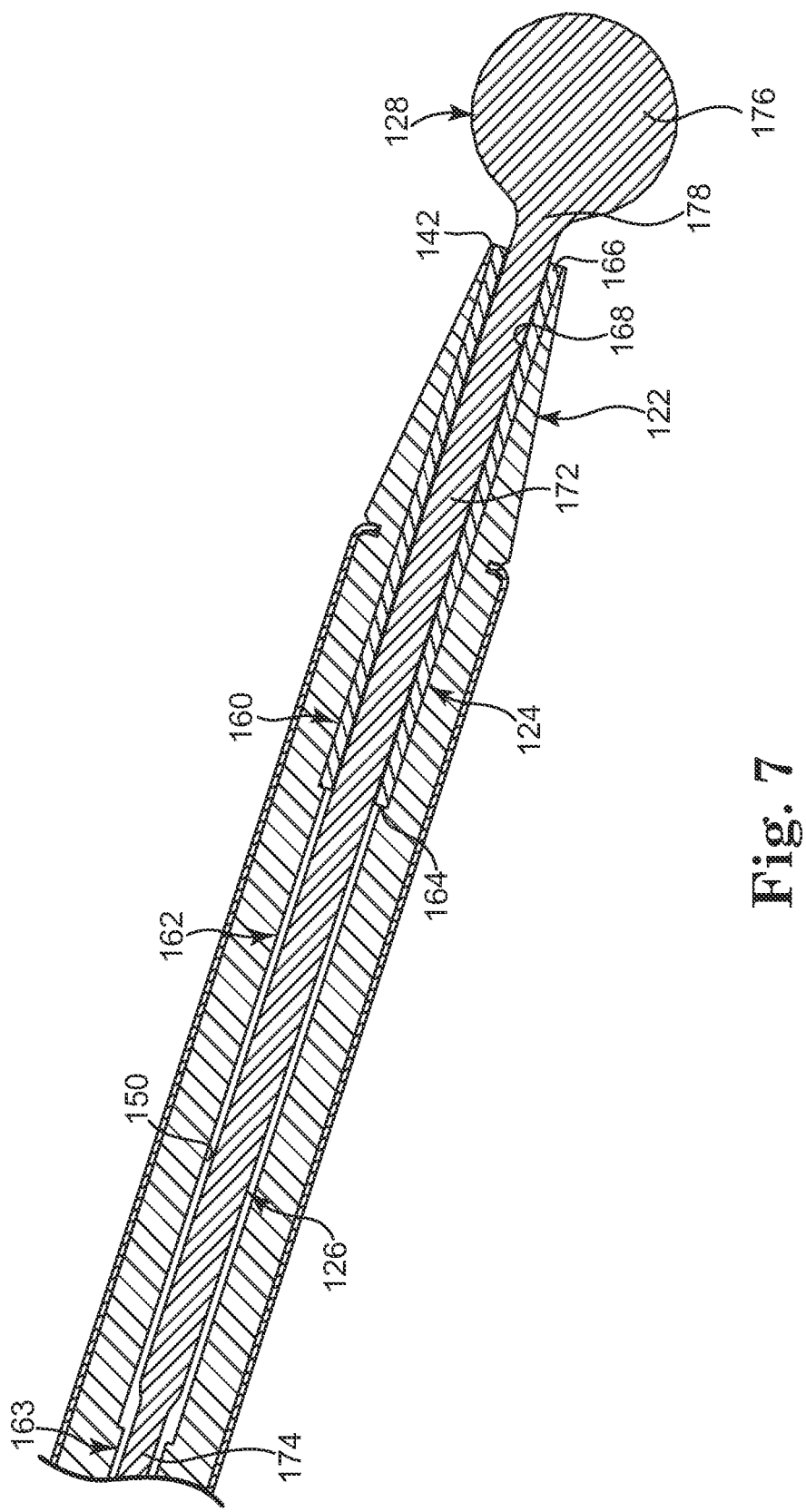
FIG. 7 is an enlarged cross-sectional view of the surgical cutting instrument of FIG. 5.

With reference to FIG. 7, the outer tube 122 defines, in some embodiments, three inner diameters at the lumen 150. For example, the lumen 150 includes a first segment 160 at a first diameter, a second segment 162 at a second diameter, and a third segment 163 at a third diameter. The first segment 160 originates at the distal end 142 and extends proximally through the distal region 146. The second segment 162 extends proximally from the first segment 160 toward the intermediate region 148. The third segment 163 proximally from the second segment 162 through the intermediate region 148 and the proximal region 144 to the proximal end 140 (FIG. 5).

The first segment 160, including the first diameter, can be adapted to receive at least a portion of the bearing sleeve 124. For example, the first segment 160 is optionally sized and shaped, or otherwise adapted, to receive the bearing sleeve 124 in a press fit. The second and third segments 162, 163 are sized and shaped, or otherwise adapted, to receive a portion of the inner wire assembly 126. By way of reference, in one non-limiting embodiment, the first segment 160 has a diameter of about 0.060 inch (1.52 mm). It should be understood that a number of other dimensions (greater or lesser) are also contemplated.

The bearing sleeve 124 is substantially similar to the bearing sleeve 24 (FIG. 2) previously described. The bearing sleeve 124 defines a proximal terminus 164 and a distal terminus 166 with an inner passage 168 extending from the proximal terminus 164 to the distal terminus 166. Generally, the bearing sleeve 124 defines a bearing surface along the inner passage 168. Additionally, the bearing sleeve 124 is adapted to be inserted into the outer tube lumen 150 at the distal end 142 of the outer tube 122. For example, the bearing sleeve 124 is optionally adapted to be press fit, or otherwise define an interference fit, within the outer tube lumen 150 at the distal end 142 of the outer tube 122.

Figure 6:
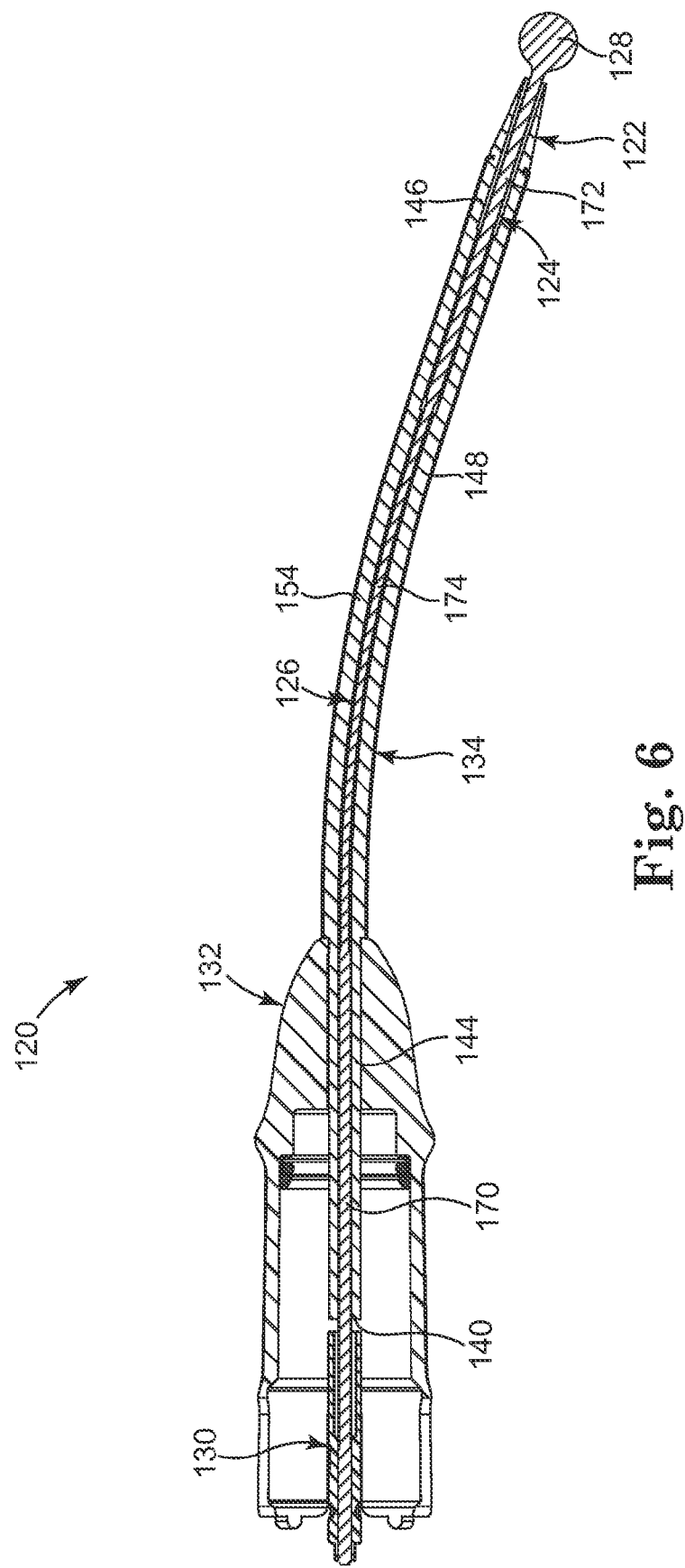
FIG. 6 is a cross-sectional view of a surgical cutting instrument in accordance with principles of the present invention.

With reference to FIG. 6, the inner wire assembly 126 defines a proximal section 170, a distal section 172, and an intermediate section 174, the intermediate section 174 between the proximal section 170 and the distal section 172. As described above with reference to the surgical cutting instrument 20 (FIG. 2), the intermediate section 174 can be more flexible than at least one of the proximal section 170 and the distal section 172. For example, the intermediate section 174 optionally defines a substantially smaller diameter than, and/or is formed of a material(s) different from, one or both of the proximal section 170 and the distal section 172 in order to provide relatively more flexibility to the intermediate section 174.

With reference to FIG. 7, the cutting tip 128 is substantially similar to the cutting tip 28 (FIG. 1) previously described, and includes a cutting bur 176 and an attachment end 178. In some embodiments, the distal section 172 of the inner wire assembly 126 is connected to the attachment end 178 by integrally forming the distal section 172 of the inner wire assembly 126 and the cutting tip 128 as shown. For example, the inner wire assembly 126 and the cutting tip 128 can be machined from a single piece of stock material. However, other methods of connection are also contemplated. For example, the cutting tip 128 can be separately formed and subsequently attached to a wire otherwise defining a remainder of the inner wire assembly 126.

With reference to FIGS. 6 and 7, the coupling chuck 130, the housing 132, and the evaporative cooling sleeve 134 are substantially similar to the coupling chuck 30, the housing 32, and the evaporative cooling sleeve 34 (FIG. 2), respectively. In general terms, assembly of the surgical cutting device 120 includes disposing the bearing sleeve 124 in the outer tube lumen 150. In turn, the inner wire assembly 126 is coaxially disposed in the outer tube 122 and the bearing sleeve 124 (as secured in the outer tube 122). A portion of the proximal section 170 of the inner wire assembly 126 projects proximally from the proximal end 140 of the outer tube 122 and a portion of the distal section 172 projects distally from the distal end 142 of the outer tube 122 with the cutting tip 128 secured thereto. The evaporative cooling sleeve 134 is optionally provided and is secured or formed about the outer tube 122. The housing 132 receives and maintains the proximal region 144 of the outer tube 122 and the coupling chuck 130, with the coupling chuck 130 connected to the proximal section 170 of the inner wire assembly 126.

The assembly of the surgical cutting instrument 120 toward the distal region 146 of the outer tube 122 is described in more detail with reference to FIG. 7. As previously described, the bearing sleeve 124 is disposed in the first segment 160 of the outer tube lumen 150. For example, the bearing sleeve 124 is optionally substantially the same length as the first segment 160 of the lumen 150 such that when the bearing sleeve 124 is inserted into the outer tube lumen 150, the bearing sleeve 124 and the distal end 142 of the outer tube 122 are substantially coterminous. In turn, at least a portion of the distal section 172 of the inner wire assembly 126 is disposed in the inner passage 168 of the bearing sleeve 124 and extends distally from the outer tube 122 and the bearing sleeve 124. The distal section 172 of the inner wire assembly 126 can be maintained by the bearing sleeve 124 such that the distal section 172 of the inner wire assembly 126 does not contact the inner surface 152 of the outer tube 122 upon rotation of the inner wire assembly 126 and/or while the inner wire assembly 126 is stationary.

For example, although the distal section 172 of the inner wire assembly 126 projects proximally from the bearing sleeve 124 into the second segment 162 of the outer tube lumen 150, the bearing sleeve 124 serves to maintain the distal section 172 of inner wire assembly 126 such that any contact (incidental or intentional) is at the interface between the bearing sleeve 124 and the distal section 172, rather than contact between outer tube 122 and the distal section 172. In particular, the inner passage 168 of the bearing sleeve 124 defines a smaller diameter than the second diameter of the lumen second segment 162. In this manner, the effective inner diameter includes a step from the inner passage 168 to the second segment 162 of the outer tube lumen 150. A stepwise or other type of increase in relative size of the second diameter relative to the diameter of the inner passage 168 helps ensure that the distal section 172 is maintained by the bearing sleeve 124 rather than being supported directly by the outer tube 122. For example, the third diameter of the third segment 163 of the outer tube lumen 150 is stepped down in size relative to the second segment 162. This helps ensure that the distal section 172 of the inner wire assembly 126 does not bind or otherwise undesirably interfere with the outer tube 122.

The distal section 172 of the inner wire assembly 126 is supported by the bearing sleeve 124 in a substantially linear configuration, or is otherwise free of overt bends or curves. As alluded to above, the distal section 172 of the inner wire assembly 126 can be substantially thicker in diameter than the intermediate section 174, such that the distal section 172 and the proximal section 174 are more rigid than the intermediate section 174, and thus provide greater structural strength and are more suited to rotation within a substantially linear, or straight, portion of the outer tube 122. As previously described, the intermediate section 174 can be substantially thinner, and therefore able to flex more easily. As such, the intermediate section 174 adapted to extend through one or more curved segments of the outer tube 122, such as the curved segment 154, and adapted to be rotated therein without undue fatiguing or resistance to rotation.

Figure 8:
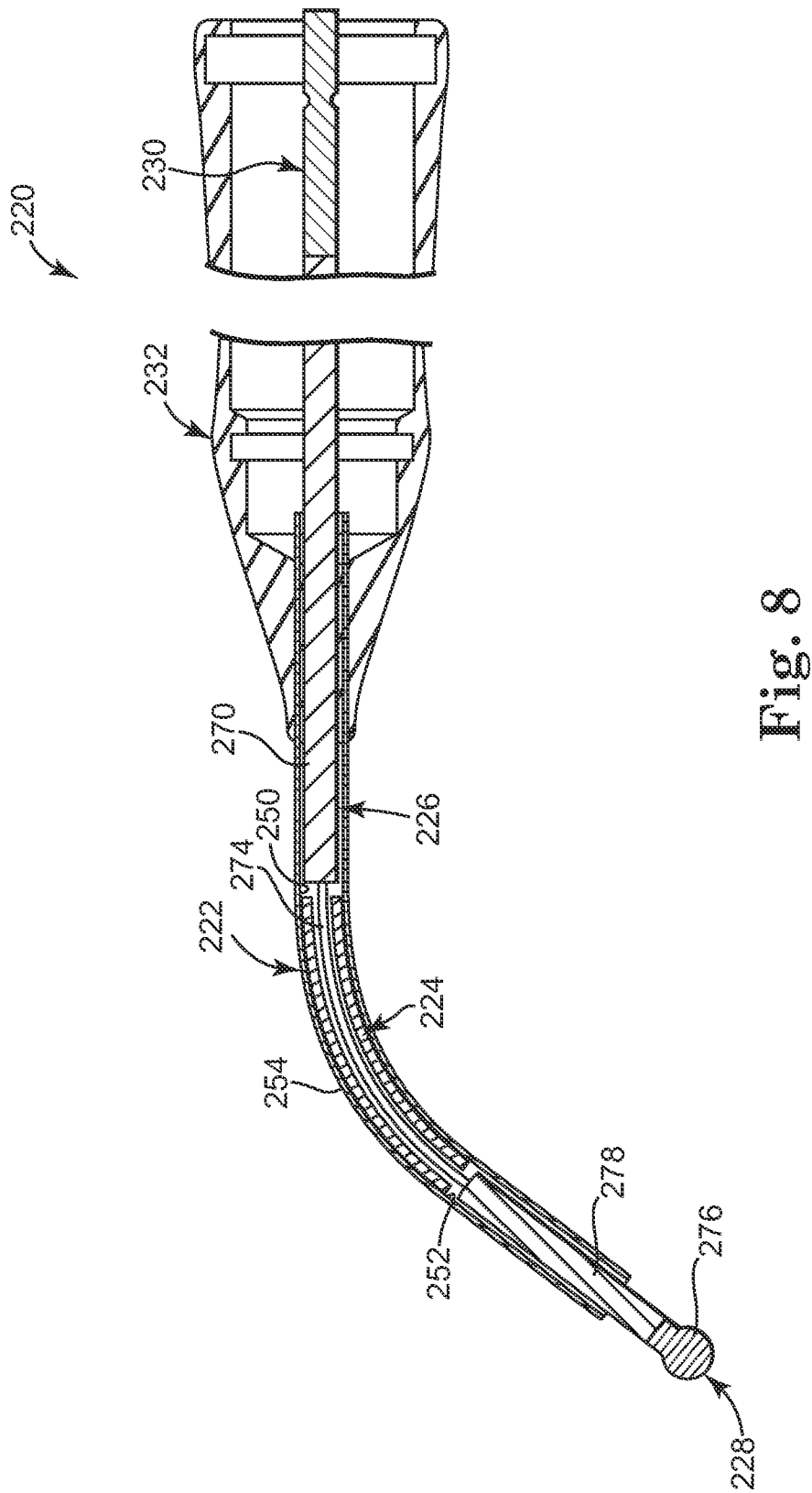
FIG. 8 is a cross-sectional view of a surgical cutting instrument in accordance with principles of the present invention.

Another surgical cutting instrument 220 in accordance with principles the present invention is described with reference to FIG. 8. The cutting instrument 220 is similar to previous embodiments and includes an outer tube 222, an inner wire assembly 226, a cutting tip 228, a coupling chuck 230, and a housing 232. Once again, the inner wire assembly 226 is coaxially disposed within a lumen 250 formed by the outer tube 222 that otherwise optionally includes a curved segment 254. Further, an intermediate tube 224 is disposed between the outer tube 222 and the inner wire assembly 226 along the curved segment 254.

The outer tube 222 optionally assumes any of the forms previously described with respect to the cutting instruments 20, 120 (FIGS. 1, 5), as can the coupling chuck 230 and the housing 232. The inner wire assembly 226 includes a first or proximal section 270 and a second or intermediate section 274. The first section 270 is optionally a rigid shaft or wire to which the coupling chuck 230 is secured or integrally formed. The second section 274 extends distally from the first section 270 and in some embodiments, is a spring wire akin to the inner wire assemblies 26, 126 previously described. That is to say, the second section 274 assume any of the forms previously described with respect to the inner wire assemblies 26, 126. The first and second sections 270, 274 can be separately formed and fastened together (e.g., laser weld, sintering, and others), or integrally formed from a single piece of stock material. Regardless, in some embodiments, the second section 274 defines a diameter less than that of the first section 270, having an axial length substantially commensurate with an arc length of the curved segment 254 of the outer tube 222.

The cutting tip 228 can include a cutting bur 276 and a shaft 278. The shaft 278 extends distally from the cutting bur 276 and is attached to the second section 274 of the inner wire assembly 226. Also, the shaft 278 can be formed as part of the inner wire assembly 226, for example as a distal section of the inner wire assembly 226, with the cutting bur 276 subsequently attached thereto. For example, the shaft 278 is optionally of an identical construction as the first section 270. Even further, the cutting tip 228 and the inner wire assembly 226 can be integrally formed. Regardless, the second section 274 is formed to have a diameter less than that of the shaft 278.

The diameter of the second section 274 can be smaller than that of the first section 270 and the shaft 278, as the second section 274 does not need to support the bending load induced by the cutting bur 276. This construction has the potential for allowing a reduced radius second section 274 at the curved segment 254 (along which the second section 274 resides upon final assembly) and serves to reduce the friction load/heat in the curved segment 254.

The intermediate tube 224, also described as a bearing sleeve 224, is provided between the second section 274 and the outer tube 222 to support the second section 274 upon rotation of the inner wire assembly 226. The intermediate tube 224 can be formed of a PTFE material; also, other flexible tubing materials can be employed. The intermediate tube 224 can be substantially inflexible and resistant to bending. The intermediate tube 224 acts, with some configurations in accordance with principles of the present invention, to modify the effective inner diameter of the outer tube 222, such that the effective inner diameter of the outer tube 222 is stepped down in the second section 274.

During use, the surgical cutting instrument 220 operates in a manner highly similar to previous embodiments. In particular, a motor (not shown) rotates the inner wire assembly 226 relative to the outer tube 222 such that a rotating journal bearing is created between at least a portion of the inner wire assembly 226 and an inner surface 252 of the outer tube 222. A grease or other lubricant is optionally disposed between portions of the inner wire assembly 226 and the outer tube 222, for example along the first section 270 and/or the shaft 272 of the cutting tip 228 such that at high rotational speeds, a hydrodynamic bearing is established along the outer tube 222. Similar to previous embodiments, then, the surgical cutting instrument 220 is adapted to provide a nominal rotational speed of 80,000 RPM with a low profile, curved outer tube 222 assembly.

Figure 9A:
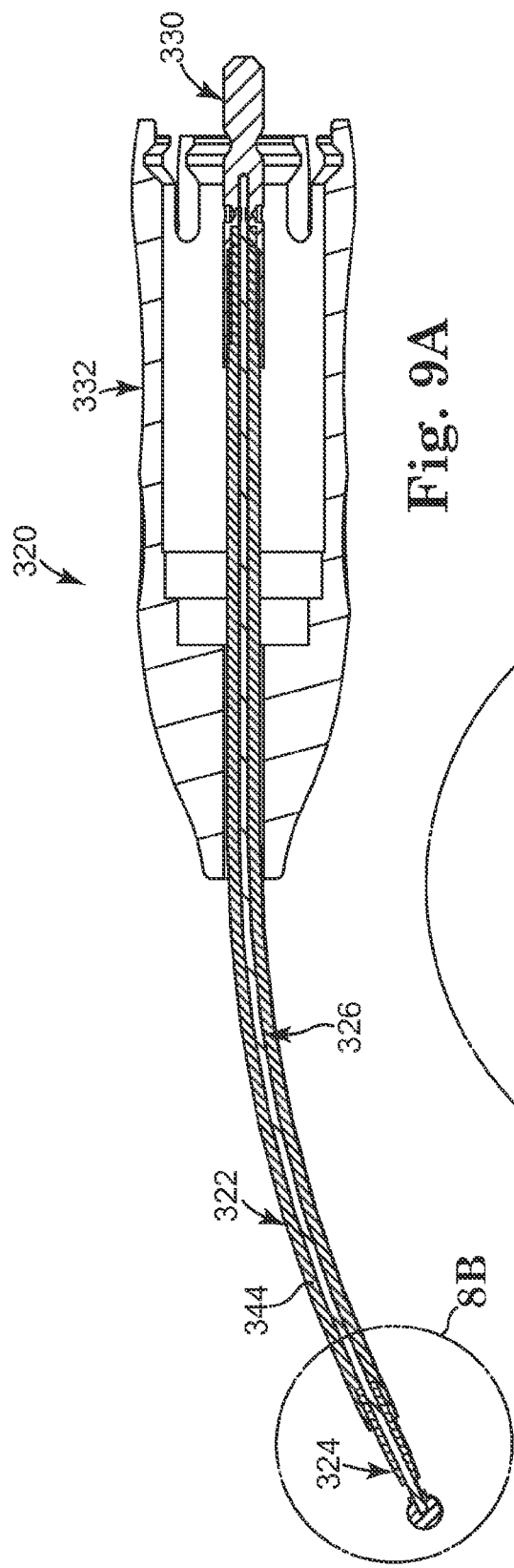
FIG. 9A is cross-sectional view of a surgical cutting instrument in accordance with principles of the present invention.
Figure 9B:
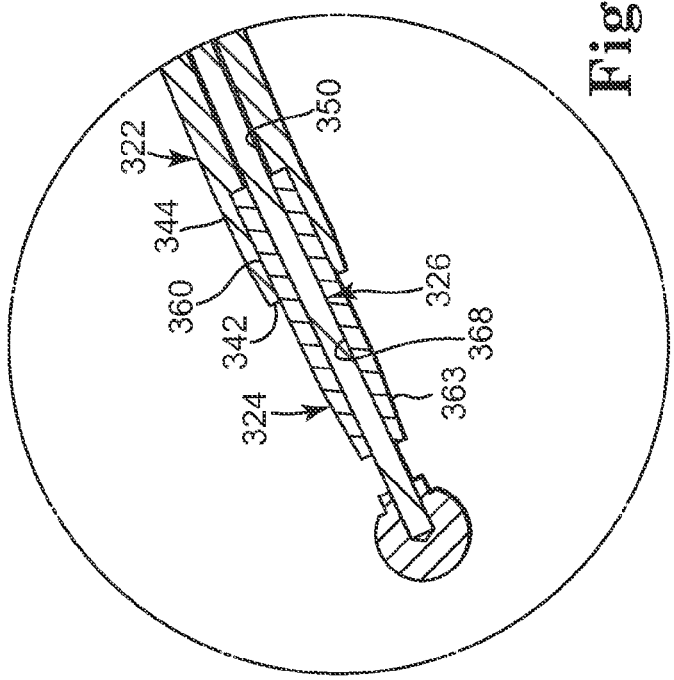
FIG. 9B is an enlarged cross-sectional view of the surgical cutting instrument of FIG. 9A designated by the circle 9B.

Another surgical cutting instrument 320 in accordance with principles of the present invention is shown in FIGS. 9A and 9B. The surgical cutting instrument 320 incorporates sealing features which can be incorporated into one or more of the surgical cutting instruments described above to minimize flow of material into or out of the outer tube and/or act as a bearing surface. For example, FIG. 9A is a side, cross-sectional view of the surgical cutting instrument 320 akin to embodiments described in association with the surgical cutting instruments 20, 120, 220. The surgical cutting instrument 320 includes an outer tube 322, a sealing tip 324, also described as a bearing sleeve 324, an inner wire assembly 326, a cutting tip 328, a coupling chuck 330, and a housing 332. The sealing tip 324 is attached to, and extends distally from, a distal region 346 of the outer tube 322, and provides a bearing/sealing surface that more closely approximates an outer diameter of the inner wire assembly 326 of the surgical cutting instrument 320, thus limiting possible intake and/or release of material from/to the surgical site.

The sealing tip 324 can be formed of a ceramic or polymer material, for example sapphire, and exhibits enhanced hardness and surface finish as compared to the outer tube 322. Thus, the sealing tip 324 has elevated wear characteristics, increasing a life of a bearing formed between the sealing tip 324 and the inner wire assembly 326. Further, ceramic materials can be more readily manufactured to exacting tolerance requirements as compared to steel (as is otherwise optionally used for the outer tube 322) such that an inner lumen or inner passage 368 of the sealing tip 324 has a diameter less than a diameter of the lumen 350 of the outer tube 322, resulting in a reduced diametrical clearance relative to the inner wire assembly 326. This reduced clearance, in turn, further prevents material from entering and/or exiting the outer tube 322. For example, the lumen 368 of the sealing tip 324 can be manufactured to provide a diametrical clearance relative to the inner wire assembly 326 in the range of from about 0.005 mm to about 0.01 mm, although other dimensions are also acceptable.

The sealing tip 324 can be assembled to the outer tube 322 in a variety of fashions. For example, the outer tube 322 can form an internal aperture or counter-bore 360 at a distal end 342 thereof, having a diameter adapted to receive an outer diameter of the sealing tip 324 via a close slip fit, or a press fit. With this configuration, an adhesive or retaining compound (not shown) optionally secures the sealing tip 324 to the outer tube 322. Regardless, in one embodiment, the sealing tip 324 and/or the outer tube 322 are configured to provide a longitudinal interface length of at least 1.5× a diameter of the sealing tip 324 to maintain squareness and straightness. Because the sealing tip 324 is longitudinally straight, an overall length is optionally relatively short when employed with a curved configuration of the outer tube 322. To provide a sufficient bearing surface, the sealing tip 324 has a length in the range of from about 8 mm to about 14 mm although other dimensions are contemplated. Finally, the sealing tip 324 has an outer diameter commensurate with, optionally less than, that of the outer tube 322, and can form a distal taper 363. For example, the sealing tip 324 can taper from about 1.5 mm to about 2.5 mm in outer diameter, although other dimensions are also acceptable.

Embodiments of surgical cutting instruments of the present invention provides a marked improvement over previous designs. By eliminating a need for a ball bearing assembly in conjunction with desired material selections and processing techniques, the outer support tube can have an outer diameter significantly less than other available surgical instruments along with optimally located and sized curved section(s), while providing requisite stiffness. Further, material selection and, where desired, lubricant, allows for long-term high-speed rotation (on the order of 80,000 RPM) with minimal instrument wear and heat build-up. Finally, embodiments of the surgical cutting instrument of the present invention require a minimal number of components, thus reducing costs and assembly time.

Due to the high speeds of operation, curved, low profile features, embodiments of the surgical cutting instrument of the present invention can be used in a wide variety of surgical applications. One field of possible applications includes numerous neuro-otology procedures, such as cochlear implant, vestibular nerve section, facial nerve decompression, endolymphatic hydrops, and removal of tumors of the ear including acoustic neuroma surgery (e.g., middle and posterior fossa approaches), drainage of petrous apex cysts, and mastoidectomies, to name but a few. In addition, the surgical cutting instrument of the present invention can be used for a variety of other bodily procedures, such as those relating to sinus surgery, removal of bone spurs on the vertebrae, removal of arthritic bone spurs throughout the body, spinal disc surgery, knee surgery, hip surgery, orthopedic surgical procedures, and others. In more general terms, the surgical cutting instrument can be employed to remove, resect, cut, or debulk any bodily material (e.g., tissue, bone, etc.).

Embodiments of the high speed surgical cutting instrument of the present invention can be employed in the debulking and/or resecting of bone. For example, embodiments including a larger cutting tip (e.g., having a diameter of greater than about 2 mm, from about 3 mm to about 4 mm, or about 3 mm or greater) can be employed to perform the debulking operation. It should also be understood that embodiments including such larger cutting can also be employed to perform a resecting operation or a portion thereof. Conversely, embodiments including a cutting tip having a diameter of about 2 mm or less can be employed to perform the resecting operation, or even the debulking operation or a portion thereof as desired. During debulking and/or resecting, the surgical cutting instrument 20, 120, 220, 320 is deployed and operated (e.g., at speeds of at least 50,000 RPM, including speeds of about 80,000 RPM) to resect/debulk the bone through the facial recess.

Embodiments of the surgical cutting instrument of the present invention with the curved configuration optionally protect the facial nerve as the outer tube extends into the facial recess, thus minimizing exposure of the facial nerve to the rotating inner wire that might otherwise unexpectedly contact the facial nerve and/or cause thermal damage. Further, the curved, minimal outer diameter features of the surgical cutting instrument of the present invention affords the surgeon vastly improved visibility of the surgical site as compared to conventional cutting devices.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A surgical cutting instrument for use with a motor having a drive mechanism, the instrument comprising:
   an outer tube defining a proximal end, a distal end, a proximal region extending to the proximal end, a distal region extending to the distal end, and a lumen extending from the proximal end to the distal end;
   a bearing sleeve being substantially tubular in shape and defining a proximal terminus, a distal terminus, and an inner passage extending from the proximal terminus to the distal terminus, at least a portion of the bearing sleeve secured within the lumen of the outer tube with a plurality of exteriorly projecting ribs facing an inner surface of the outer tube;
   an inner wire assembly defining a proximal section and a distal section, the inner wire assembly extending through the lumen of the outer tube and through the inner passage of the bearing sleeve;
   a cutting tip connected to the distal section of the inner wire assembly;
   a coupling chuck adapted for connection to a drive mechanism of a motor, the coupling chuck being connected to the proximal section of the inner wire assembly; and
   a housing maintaining the proximal region of the outer tube and the coupling chuck, the housing being adapted for connection to a motor.

2. The instrument of claim 1, wherein the bearing sleeve has an inner bearing surface bounding the inner passage, the instrument further comprising:
   a grease lubricant disposed between the inner wire assembly and the inner bearing surface of the bearing sleeve.

3. The instrument of claim 1, wherein the bearing sleeve has an inner bearing surface bounding the inner passage of the bearing sleeve, and further wherein the instrument is configured such that upon final assembly and rotation of the inner wire assembly, a rotating journal bearing is established between the outer surface of the inner wire assembly and the inner bearing surface.

4. The instrument of claim 1, wherein a diameter of the inner passage of the bearing sleeve is less than an inner diameter of at least a portion of the lumen at the distal region of the outer tube.

5. The instrument of claim 1, wherein a diameter of the inner passage of the bearing sleeve is substantially the same as an inner diameter of at least a portion of the lumen at the distal region of the outer tube.

6. The instrument of claim 1, wherein the lumen of the outer tube extends along a first segment at a first diameter and a second segment at a second diameter, the second segment being formed proximal the first segment, and further wherein the first diameter is greater than the second diameter.

7. The instrument of claim 6, wherein the bearing sleeve is received entirely within the first segment of the lumen.

8. The instrument of claim 1, wherein the lumen of the outer tube includes a first segment having a first diameter, a second segment having a second diameter, the second segment being defined proximal the first segment, and a third segment having a third diameter, the third segment defined proximal the second segment, and further wherein the first diameter is greater than the second diameter, and the second diameter is greater than the third diameter.

9. The instrument of claim 1, wherein the inner wire assembly further defines an intermediate section between the proximal and distal sections that otherwise each define an outer diameter that is greater than an outer diameter of the intermediate section, and further wherein at least a portion of the distal section is disposed within the inner passage of the bearing sleeve.

10. The instrument of claim 1, wherein the distal terminus of the bearing sleeve is substantially coterminous with the distal end of the outer tube.

11. The instrument of claim 1, wherein the distal region of the outer tube extends at an angular offset relative to the proximal region of the outer tube.

12. The instrument of claim 1, wherein the bearing sleeve is formed of a non-metallic material.

13. The instrument of claim 1, wherein an air gap is established between an exterior surface of the bearing sleeve and the interior surface of the outer tube.

14. The instrument of claim 1, wherein the bearing sleeve is non-rotatably mounted to the outer tube.

15. The instrument of claim 1, wherein the bearing sleeve has a length in the range of 0.27-0.65 inch.

16. The instrument of claim 1, further comprising a cooling sleeve disposed on an exterior of the outer tube, wherein the cooling sleeve is a tubular body separate and distinct from the housing.

17. A surgical cutting instrument for use with a motor having a drive mechanism, the instrument comprising:
- an outer tube defining a proximal end, a distal end, a proximal region extending to the proximal end, a distal region extending to the distal end, and a lumen extending from the proximal end to the distal end;
- a bearing sleeve being substantially tubular in shape and defining a proximal terminus, a distal terminus, and an inner passage extending from the proximal terminus to the distal terminus, at least a portion of the bearing sleeve secured within the lumen of the outer tube;
- an inner wire assembly defining a proximal section and a distal section, the inner wire assembly extending through the lumen of the outer tube and through the inner passage of the bearing sleeve;
- a cutting tip connected to the distal section of the inner wire assembly;
- a coupling chuck adapted for connection to a drive mechanism of a motor, the coupling chuck being connected to the proximal section of the inner wire assembly;
- a housing maintaining the proximal region of the outer tube and the coupling chuck, the housing being adapted for connection to a motor; and
- a tubular cooling sleeve disposed on an exterior of the outer tube, the cooling sleeve having a first end and an opposing second end, the first end disposed proximal to the housing and the second end disposed along the distal region of the outer tube.

18. The instrument of claim 17, wherein the cooling sleeve is formed of a fabric material.

19. The instrument of claim 18, wherein the cooling sleeve is formed of uncoated nylon.

20. The instrument of claim 17, wherein the cooling sleeve is constructed of one of a braided tube and a coil of thread.

* * * * *